United States Patent [19]
Levitt et al.

[11] Patent Number: 6,070,587
[45] Date of Patent: Jun. 6, 2000

[54] ONE-PIECE OPTHALMIC DRAPE AND METHODS

[75] Inventors: Yolla B. Levitt, Mendota Heights, Minn.; Dennis L. Baker, Houlton, Wis.; Camille M. Hildebrandt, Woodbury, Minn.; Mary K. Reed, Brookings, S. Dak.; Robert A. Davis, Cottage Grove, Minn.

[73] Assignee: 3M Innovative Properties Company, St. Paul, Minn.

[21] Appl. No.: 08/941,820

[22] Filed: Oct. 1, 1997

[51] Int. Cl.⁷ .................................................. A61B 19/00
[52] U.S. Cl. ............................................ 128/849; 128/853
[58] Field of Search ................................... 128/849–856

[56] References Cited

U.S. PATENT DOCUMENTS

| Re. 24,906 | 12/1960 | Ulrich ........................................ 206/59 |
| 1,044,698 | 11/1912 | Sideman . |
| 2,294,593 | 9/1942 | Bailey .......................................... 2/174 |
| 3,068,863 | 12/1962 | Bowman ................................... 128/132 |
| 3,410,266 | 11/1968 | Krzewinski et al. .................... 128/132 |
| 3,561,439 | 2/1971 | Bayer ........................................ 128/132 |
| 3,565,067 | 2/1971 | Bayer et al. ............................. 128/132 |
| 3,667,458 | 6/1972 | Krebs ....................................... 128/132 |
| 3,736,928 | 6/1973 | Andersson et al. .................. 128/146.2 |
| 3,750,664 | 8/1973 | Collins ................................. 128/132 D |
| 3,766,913 | 10/1973 | Balin ........................................ 128/132 |
| 3,923,052 | 12/1975 | Zoephel ............................... 128/132 D |
| 3,930,497 | 1/1976 | Krebs et al. ............................. 128/132 |
| 4,033,341 | 7/1977 | Scrivens .................................. 128/132 |
| 4,089,331 | 5/1978 | Hartigan et al. ......................... 128/132 |
| 4,275,720 | 6/1981 | Wichman ................................. 128/132 |
| 4,316,456 | 2/1982 | Stoneback ............................... 128/132 |
| 4,323,062 | 4/1982 | Canty ....................................... 128/132 |
| 4,711,236 | 12/1987 | Glassman ................................ 128/132 |
| 4,739,753 | 4/1988 | Brehm ................................. 128/200.24 |
| 4,873,997 | 10/1989 | Marshall ................................. 128/849 |
| 4,966,168 | 10/1990 | Glassman ............................... 128/853 |
| 5,038,798 | 8/1991 | Dowdy ..................................... 128/849 |
| 5,109,873 | 5/1992 | Marshall ................................. 128/849 |
| 5,127,423 | 7/1992 | Draeger ................................... 128/849 |
| 5,140,997 | 8/1992 | Glassman ................................ 128/849 |
| 5,345,946 | 9/1994 | Butterworth ............................. 128/853 |
| 5,361,780 | 11/1994 | Kellan ...................................... 128/853 |

FOREIGN PATENT DOCUMENTS

| AU-A-63114/90 | 3/1991 | Australia . |
| 1 187 363 | 5/1985 | Canada . |
| 2025912 | 3/1991 | Canada . |
| 0 1660124 A2 | 1/1986 | European Pat. Off. . |
| 0 420 073 A1 | 4/1991 | European Pat. Off. . |
| 0 420 073 B1 | 4/1991 | European Pat. Off. . |
| 780.734 | 5/1935 | France . |
| 2128904 | 10/1972 | France . |
| 2 442 047 | 6/1980 | France . |
| 89 04 426 U | 5/1989 | Germany . |
| 3931803 C1 | 5/1990 | Germany . |
| WO 89/0511131 | 6/1989 | WIPO . |
| WO 94/24954 | 11/1994 | WIPO . |

*Primary Examiner*—Michael A. Brown
*Attorney, Agent, or Firm*—Gary L. Griswold; Eloise J. Maki; Stephen W. Bauer

[57] ABSTRACT

An ophthalmic drape that can easily be adhered to both the upper and lower margins of the eye without requiring the use of separate instruments for cutting and adjusting. The drape includes a sheet of material with an aperture positioned away from the periphery of the sheet. The drape has two fields of skin compatible adhesive, one on one side of the sheet near the aperture, the other on the other side of the sheet near the periphery. Once the first field of skin compatible adhesive has been adhered to one of the patient's eyelids, the section of the drape supporting the second field of skin compatible adhesive can be folded upwards and doubled back on the drape. The second field of skin compatible adhesive, which had been side away from the patient before folding, is turned side towards the patient after folding. The second field of skin compatible adhesive is then conveniently positioned to be adhered to the remaining eyelid of the patient.

20 Claims, 11 Drawing Sheets

ONE-PIECE OPTHALMIC DRAPE AND METHODS

The invention relates generally to surgical drapes, and more specifically to ophthalmic drapes having adhesive portions that allow them to be adhered to the skin adjacent the eye, and methods of manufacturing and applying such drapes.

BACKGROUND OF THE INVENTION

In order to perform surgery on the eye it is frequently desirable to apply a surgical drape to the patient, first to isolate the eyelashes and eyelids from the surgical site to improve exposure of the eye, and provide a sterile drape surface to reduce the chance of infection. For example, in refractive surgery, draping may be primarily performed to pull eyelids and eyelashes away from the eye, and keep them out of the way of surgical instruments such as microkeratomes.

One product used for this purpose is the Model 1020 ophthalmic drape commercially available from the Minnesota Mining and Manufacturing Company, St. Paul, Minn. This drape includes a sheet of material having a generally round aperture in roughly the center. A field of skin compatible adhesive contacts a portion of one side of the sheet adjacent this aperture. This adhesive allows the drape to be adhered around the patient's eye, and the rest of the sheet drapes down over the patient's head, hair and face to provide a sterile surface over these areas.

A difficulty arises in that the eye is a delicate structure and the eyelids are very flexible and not the same size and shape in different individuals. In actual practice, sometimes medical practitioners find it inconvenient to conform the margins of the aperture to the edges of a particular patient's eyelids. When this occurs, one expedient that is known to some practitioners is to cut the drape, either partly or else completely into two sections, to relieve the tension in stretched areas or to prevent bunching of the adhesive, and allow the margin of the aperture to be more perfectly conformed to the margin of the patient's eye. In addition, cutting the drape before application is the preferred practice of many surgeons in order to facilitate one person applying the drape to the upper eyelid first without adhering the lower portions of the adhesive field to the lower eyelid until ready to do so.

It will be appreciated that this expedient is not without its drawbacks. Making such a cut during application will require the presence of a sterile scissors or the like. Also, making an appropriate cut is inconvenient to do while attempting to preserve the sterility of the drape.

SUMMARY OF THE INVENTION

This invention provides a method of draping the eye for ophthalmic surgery that allows a one-piece drape to be easily conformed to both lids of the eye by a single person without additional tools. This invention solves the problems discussed above by providing an ophthalmic drape that can easily be adhered to both the upper and lower margins of the eye without requiring the use of separate instruments for cutting and adjusting. This is accomplished by providing attachment surfaces on the drape for the upper and lower eyelids on very different portions of the drape. It is therefore not necessary to put a strain on one of the attachment surfaces during the application of the other attachment surface. The upper portion of this drape can be accurately positioned on the upper eyelid while the lower portion is kept away from the surgical site until ready to position the lower portion on the lower eyelid. This is accomplished with an easy-to-handle one-piece drape.

Generally, an ophthalmic drape of the invention comprises a sheet having a first and a second side, a periphery, and an aperture spaced from the periphery of the sheet. A first field of skin compatible adhesive is provided contacting a portion of the first side of the sheet adjacent the aperture, and a second field of skin compatible adhesive is provided contacting a portion of the second side of the sheet adjacent the periphery of the sheet.

Preferably, the aperture adjacent the first field of skin compatible adhesive is formed by an edge of the sheet having a curved portion approximating an eyelid, and the periphery is defined in part by an edge portion adjacent the second field of skin compatible adhesive, the edge portion having a concave curved shape approximating an eyelid.

Also, preferably, a first release liner is adhered to the first field of skin compatible adhesive, and a second release liner is adhered to the second field of skin compatible adhesive. These release liners protect the adhesives during shipping and handling, but are peeled away by the user of the drape just before application to the patient.

The first and second sides of the sheet may conveniently define a generally rectangular shape, and the sheet may be formed of polymeric film material.

In practice, therefore, once the first field of skin compatible adhesive has been adhered to one of the patient's eyelids (e.g., the upper eyelid), the section of the drape supporting the second field of skin compatible adhesive can be folded upwards and doubled back on the drape. The second field of skin compatible adhesive, which had been the side away from the patient before folding, is turned side towards the patient after folding. The second field of skin compatible adhesive is therefore conveniently available to be adhered to the other eyelid (e.g., the lower eyelid).

Generally, the method of the invention for applying an ophthalmic drape to the upper and lower eyelids of an eye of a patient comprising the following steps:

(a) providing a surgical drape comprising a sheet having a first side, a second side, a periphery, and an aperture spaced from the periphery of the sheet;

a first field of skin compatible adhesive contacting a portion of the first side of the sheet adjacent the aperture; and a second field of skin compatible adhesive contacting a portion of the second side of the sheet adjacent the periphery of the sheet;

(b) adhering one of the fields of skin compatible adhesive to one of the eyelids; and (c) folding the surgical drape so that the other field of skin compatible adhesive is turned side towards the patient; and (d) adhering the other field of skin compatible adhesive to the other eyelid.

Preferably, the aperture has a curved portion approximating the eyelid, and the periphery has a concave-curved-shaped edge portion, which approximates the shape of an eyelid, adjacent the second field of skin compatible adhesive. In this case, the step (b) of adhering one of the fields of skin compatible adhesive to one of the eyelids and the step (d) of adhering the other field of skin compatible adhesive to the other eyelid includes placing one of the curved portion and the edge portion on one of the upper and lower eyelids (e.g., placing the curved portion on the upper eyelid), and placing the other of the curved portion and the edge portion on the other of the upper and lower eyelids (e.g., the edge portion on the lower eyelid).

Also, preferably, a first release liner is adhered to the first field of skin compatible adhesive; and a second release liner is adhered to the second field of skin compatible adhesive; and the method further comprises removing the first release liner from the first field of skin compatible adhesive and removing the second release liner from the second field of skin compatible adhesive.

In another aspect of the invention, the ophthalmic drape is manufactured according to a "two-up" manufacturing process. Generally, this method makes an ophthalmic drape from an indefinite length web having first and second sides, a longitudinal direction and a width. This method comprises the following steps:

(a) applying a first field of skin compatible adhesive to the first side of the web;

(b) cutting a first opening through the first field of skin compatible adhesive and the web;

(c) applying second and third fields of skin compatible adhesive to the second side of the web laterally spaced in opposite directions from the first field of skin compatible adhesive (e.g., spaced a substantially equal distance from the first field of skin compatible adhesive);

(d) cutting a second opening through the second field of skin compatible adhesive and the web;

(e) cutting a third opening through the third field of skin compatible adhesive and the web;

(f) cutting the web in the longitudinal direction through the first opening;

(g) cutting the web twice in the lateral direction along two cut lines spaced longitudinally in opposite directions from the first, second and third openings to form two ophthalmic drapes (e.g., substantially identical mirror image ophthalmic drapes).

Preferably, the steps (b) of cutting a first opening through the first field of skin compatible adhesive and the web, (d) of cutting a second opening through the second field of skin compatible adhesive and the web, and (e) of cutting a third opening through the third field of skin compatible adhesive and the web each comprise cutting generally oval-shaped openings approximating generally the shape of an open eye, for example, by die cutting. Most preferably, the generally oval-shaped openings are cut to have a direction of elongation extending generally along the longitudinal direction of the web.

In yet another aspect of the invention, the ophthalmic drape is manufactured according to a "one-up" manufacturing process. This method makes an ophthalmic drape from an indefinite length web having opposite major surfaces, opposite side edges and a lateral direction. Generally, this method comprises the following steps:

(a) folding one side edge of the web back on itself to form a flap folded over a main portion of the web with said one side edge overlapping the main portion of the web;

(b) applying skin compatible adhesive partly on the flap and partly on the main portion of the web with said one side edge dividing the adhesive into a first adhesive field on the main portion of the web and a second adhesive field on the flap;

(c) cutting an opening through the field of skin compatible adhesive, the flap and the main portion of the web (e.g., die cutting a generally oval-shaped opening), thus forming a first opening through the main portion and an indentation in the flap;

(d) unfolding the web;

(e) cutting the web in the lateral direction to form a ophthalmic drape having a first opening and a first adhesive field adjacent the opening along one major surface, and an indentation and a second adhesive field adjacent the indentation along the other major surface.

Most preferably, after the web is unfolded, the first opening is enlarged, for example, by die cutting, in the direction toward the indentation.

If the adhesive is applied to the web by applying a strip of transfer adhesive or double-stick patch to the web, then that strip of transfer adhesive or doublestick patch is cut to separate the first and second adhesive fields from one another before the web is unfolded. This may be conveniently done by a die-cut type roller that both cuts the transfer adhesive or double-stick patch and cuts the opening through the web.

BRIEF DESCRIPTION OF THE DRAWING

The invention will be further described with reference to the drawing wherein corresponding reference characters indicate corresponding parts throughout the several views of the drawing, and wherein.

DETAILED DESCRIPTION OF PREFERRED EMBODIMENTS

Figure 1:
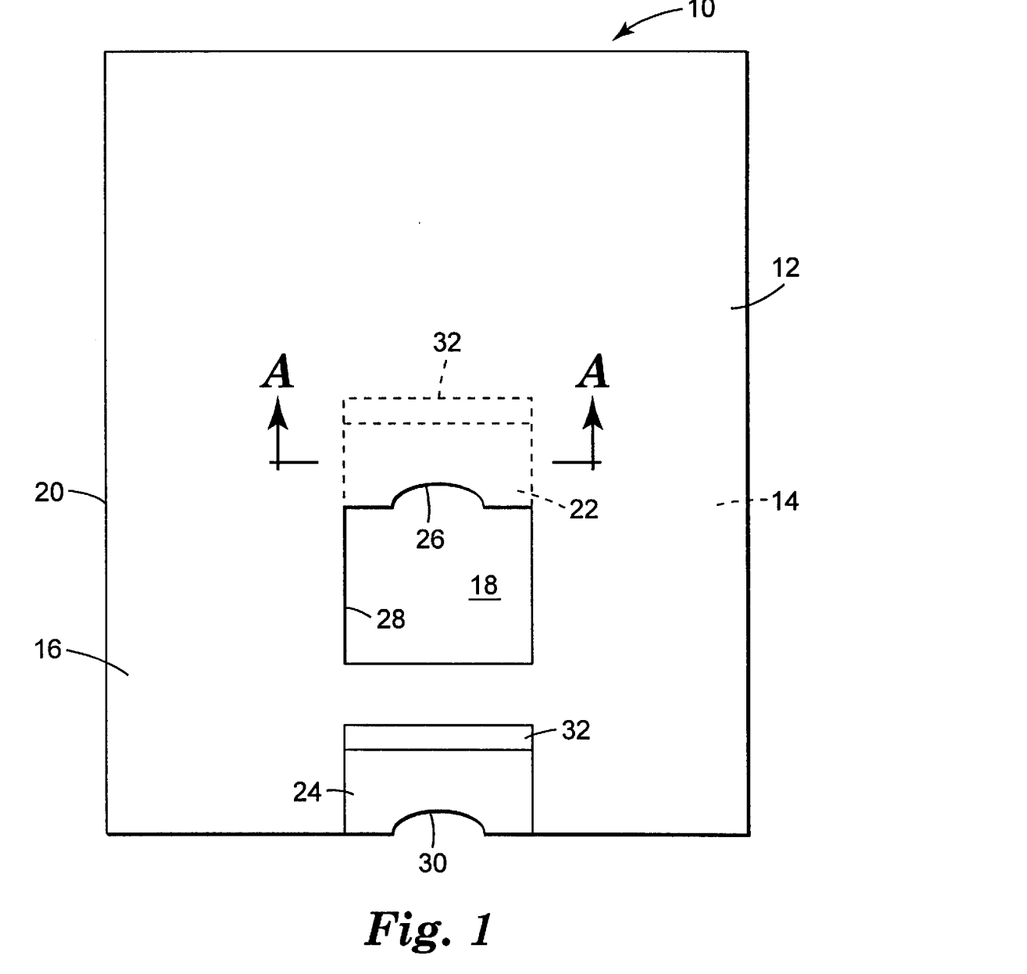
FIG. 1 is a top view of an ophthalmic drape according to the present invention.

Referring now to FIG. 1, a top view of the ophthalmic drape 10 according to the present invention is illustrated. The drape 10 includes a sheet of material 12 having a first side 14 (the underside in this view) and a second side 16 (the topside in this view). The sheet 12 has an aperture 18 therein, the aperture being at a position removed from the periphery 20 of the sheet. A first field 22 of skin compatible adhesive contacts a portion of the first side 14 of the sheet 12 adjacent the aperture 18; the first field of skin compatible adhesive is on the underside in this view, and is represented by the cross-hatched region bordered by dotted lines and the aperture. A second field 24 of skin compatible adhesive contacts a portion of the second side 16 of the sheet 12 adjacent the periphery 20 of the sheet.

A portion 26 of the margin 28 of the aperture 18 adjacent the first field of skin compatible adhesive 22 includes a curved shape, such as oval, elliptical or round, approximating the human eyelid. A portion 30 of the periphery 20 adjacent the second field of skin compatible adhesive 24 also includes a curved shape approximating the human eyelid.

Conveniently covering the second field of skin compatible adhesive 24 is a covering of release liner 32, which is shown transparent in this view for clarity. This release liner 32 protects the second field of skin compatible adhesive during shipping and handling, but is peeled away by the user of the drape just before application to the patient. A similar release liner protects the first field of skin compatible adhesive 22 on the far side of the drawing. For the convenience of the practitioner in taking a grip on release liner 32, one edge of it is permitted to extend beyond the edge of the field of skin compatible adhesive that it protects.

Figure 1A:
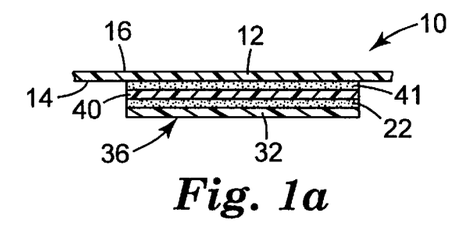
FIG. 1a is a partial cross-section view of the drape of FIG. 1 taken along section lines A—A where a double stick patch has been used to apply the skin compatible adhesive.

The first and second fields of skin compatible adhesive 22 and 24 can either be pattern coated directly on the sheet 12, or applied as a transfer adhesive, or alternatively may be applied in a pick-and-place operation as a wholly or partly coated double-stick patch. Referring now to FIG. 1a, a partial cross-section view of the drape of FIG. 1 taken along section lines A—A, where a double stick patch has been used to apply the skin compatible adhesive, is illustrated.

A double-stick patch 36 is shown adhered to the sheet 12. The patch 36 includes a backing 40 adhered to sheet 12 via adhesive 41. On the other side of backing 40 is the skin-compatible adhesive 22, which will eventually be adhered to the patient. In this view, release liner 32 can be seen protecting skin compatible adhesive 22 before use. Adhesives 22 and 41 may be the same, or may be different adhesives as convenient and compatible with the materials chosen.

Figure 1B:
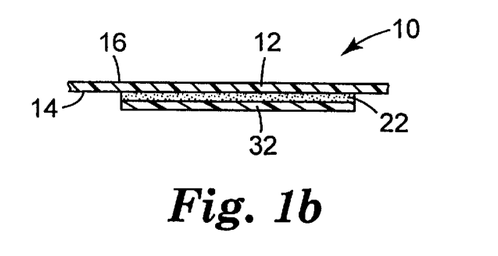
Fig. 1b is a partial cross-section view of the drape of FIG. 1 taken along section lines A—A where a transfer adhesive techniques have been used to apply the skin compatible adhesive.

Referring now to FIG. 1b, a second partial cross-section view of the drape of FIG. 1 taken along section lines A—A is illustrated so as to show the application of the field of skin compatible adhesive 22 directly to the sheet 12 as a transfer adhesive. In this case, the release liner 32 is pre-adhered to the field of skin compatible adhesive 22 before the transfer.

Figure 2:
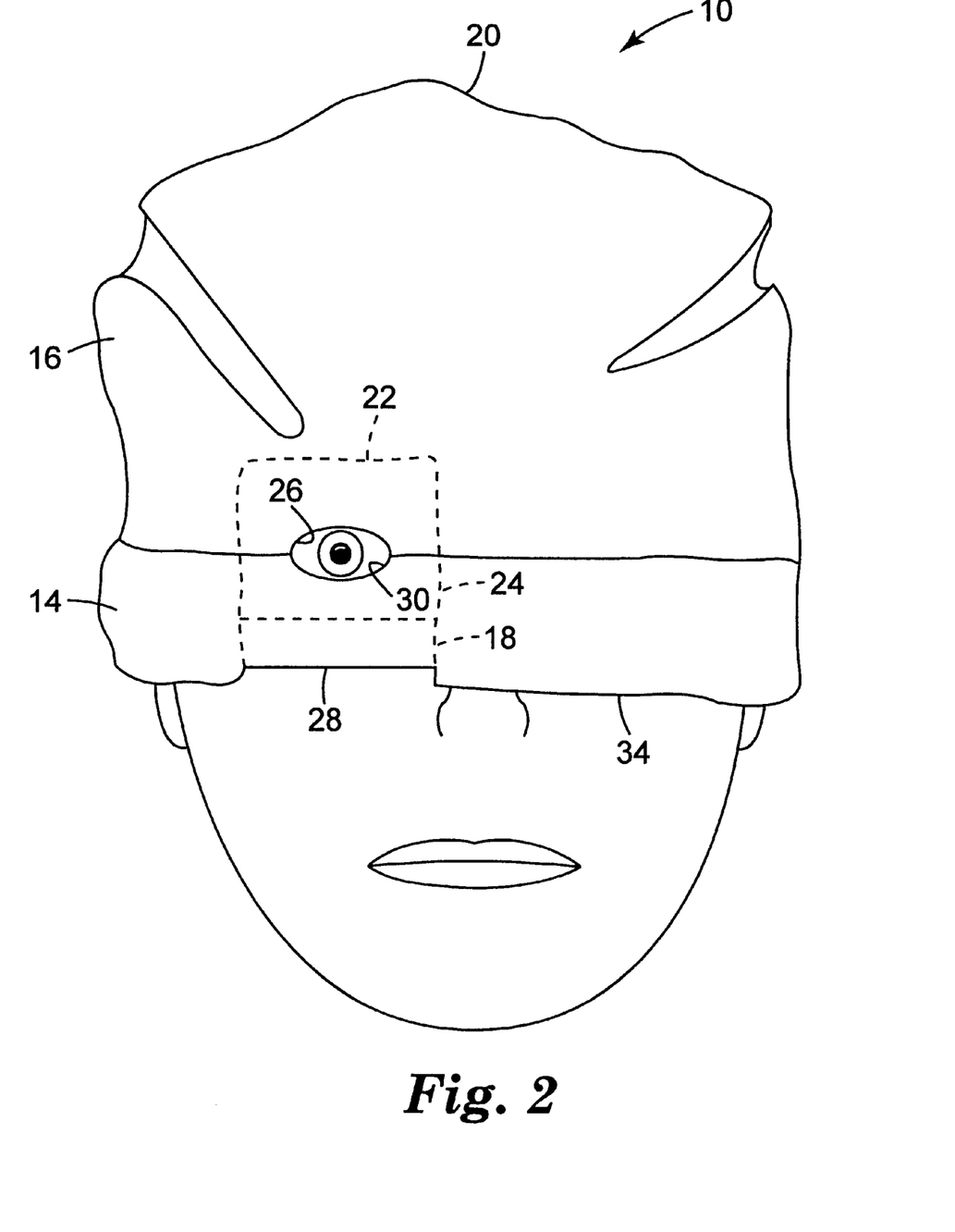
FIG. 2 is a perspective view of the drape of FIG. 1 adhered to a patient.

Referring now to FIG. 2, a perspective view of the drape 10 of FIG. 1 is illustrated as adhered to a patient. The first field of skin compatible adhesive 22 has been adhered to the patient's upper eyelid, and the sheet 12 has been folded along fold line 34 so that part of the first side 14 is turned upwards. That also causes the second field of skin compatible adhesive 24 to be turned towards the patient, and it is illustrated after having been adhered to the lower eyelid of the patient. The distance between fold line 34 and the curved portion 30 allows the second field of skin compatible adhesive 24 to be settled into place against the patient's skin without reference to the position of the first field of skin compatible adhesive 22 on the other eyelid, although it is preferred to overlap the first and second fields 22 and 24 of skin compatible adhesive.

The sheet 12 is conveniently fabricated from many sorts of polymeric film, especially polyolefin film. The use of antistatically treated polyethylene film is currently considered preferred. The skin compatible adhesive 22 and 24 is conveniently prepared from acrylate adhesive, and may be applied by various techniques, such as double-stick, pattern coating or as a transfer adhesive. A discussion of suitable compositions can be found in coassigned U.S. Pat. No. Re. 24,906 to Ulrich, which is hereby incorporated by reference. For example, the acrylate adhesive discussed as Example 5 of that document is suitable.

A double-stick adhesive typically comprises adhesive tape with the adhesive coated on both sides and a liner (e.g., a paper or polymeric liner). Pattern coating may involve a printing-type process or die coating. A transfer adhesive typically comprises an adhesive coated on a first liner (e.g., paper or polymer, such as a polyethylene film liner 32 with a silicone release coating, depending on the adhesive) that is removed before or after the transfer adhesive is put to use. A second liner (e.g., paper or polymer, such as a polyethylene film liner 32 with a silicone release coating) may be laminated to the adhesive either before or after the first liner is removed.

Figure 3A:
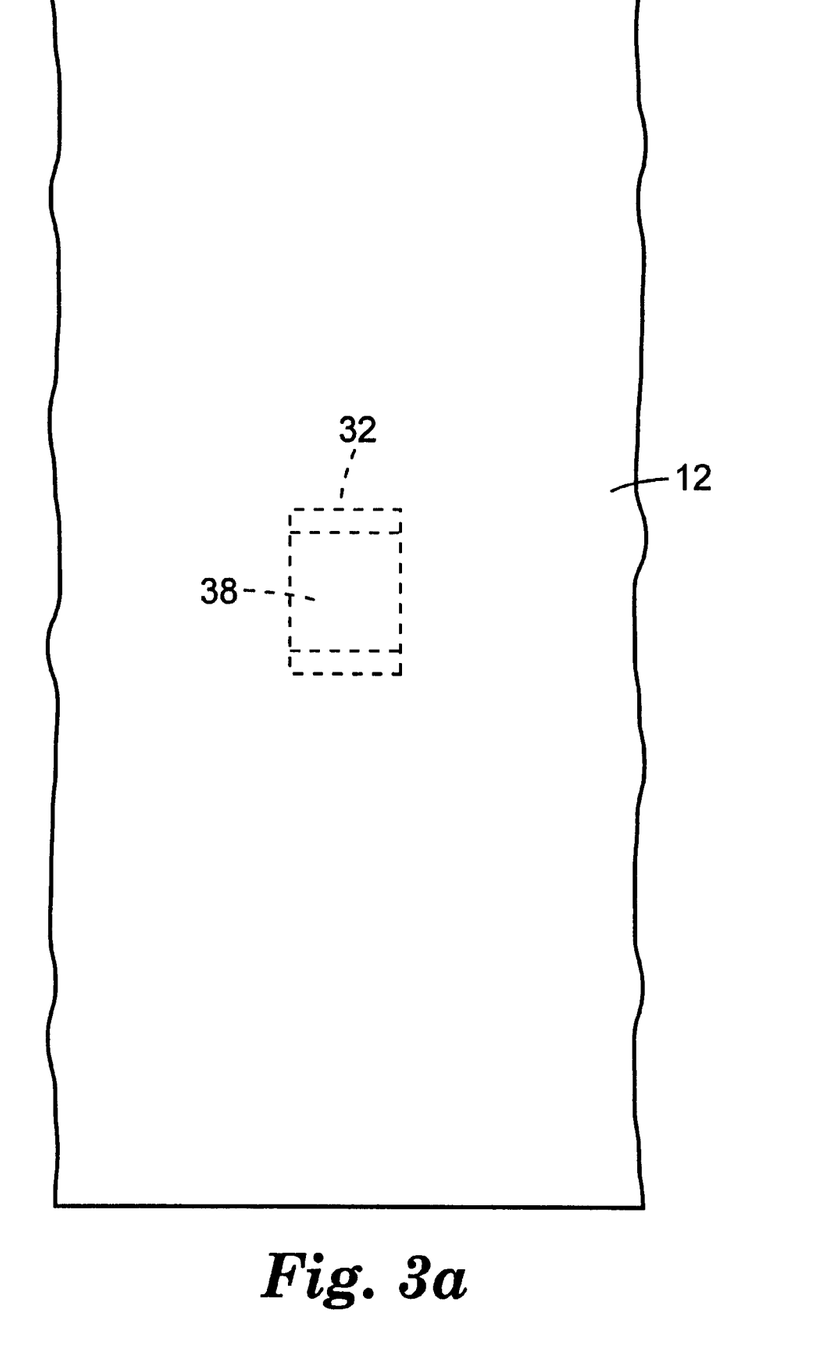
FIGS. 3a–3f are top views of a representative section of an indefinite length of sheet material at sequential stages of a "two-up" manufacturing scheme for the ophthalmic drape.

Referring now to FIGS. 3a–3f, top views of a representative section of an indefinite length web at sequential stages of a "two-up" manufacturing scheme for the ophthalmic drape 10. As used herein, the terms "longitudinal direction" means the continuous or machine direction of the web, and the "width" means the cross web or lateral direction. In FIG. 3a, an indefinite length of sheet material 12, conveniently 36 inches (91.4 cm) wide, has had adhered to it a strip of skin compatible adhesive 38 via transfer adhesive techniques. The strip 38 has conveniently been applied with release liner 32 adhered to the other side of the strip 38 with two of the ends of the release liner extending beyond the ends of the strip. Strip 38 will eventually form the second field of skin-compatible adhesive 24 on the two drapes 10 that will be formed side-by-side from this segment of the indefinite length sheet 12.

Figure 3B:
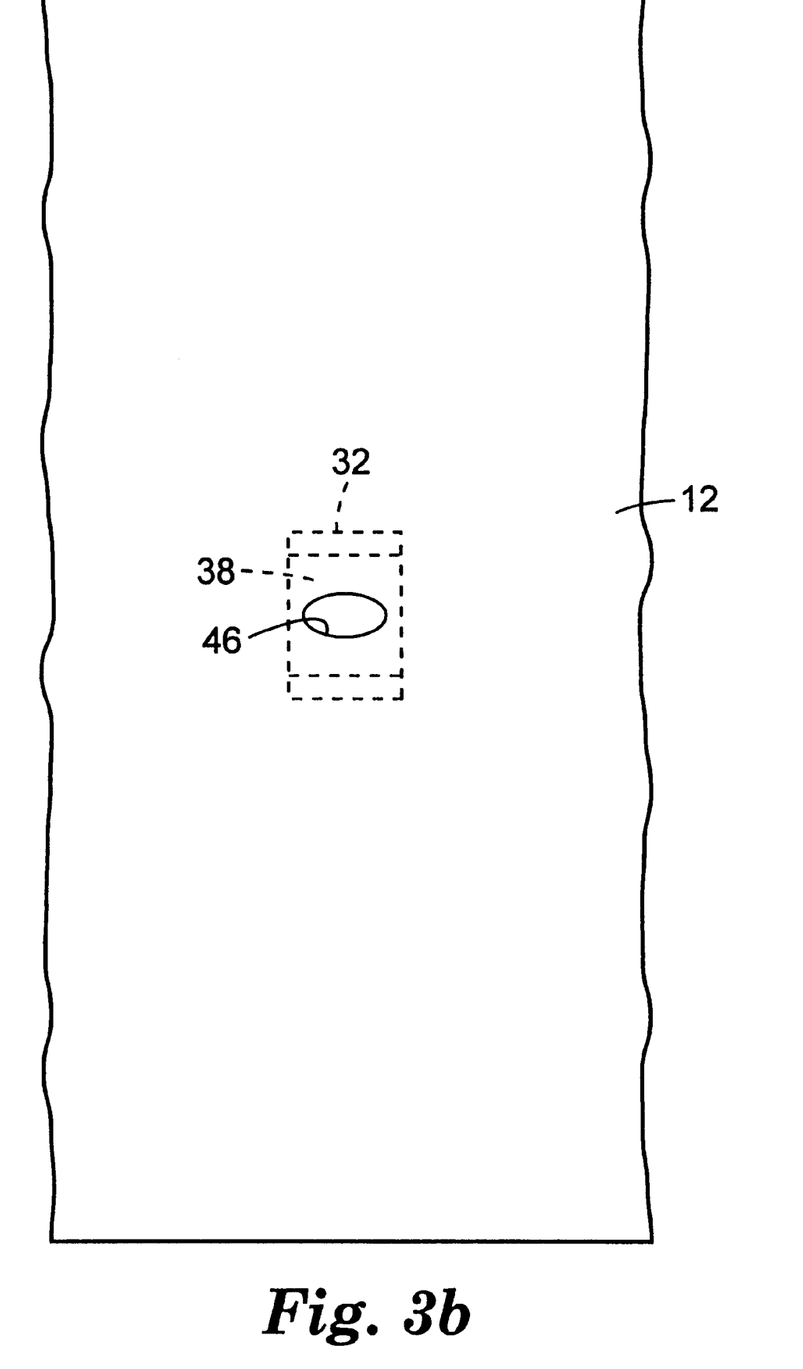

In FIG. 3b, a die cutter has punched an opening 46 that eventually will form the curved portion 30 on the two drapes 10 that will be formed from this segment of the indefinite length sheet. Once this has been done, since the remaining steps in this process must be undertaken on the other side of the indefinite length sheet, the indefinite length sheet may, if convenient, be rolled on a jumbo so that the remainder of the steps may be formed in a second pass through another converter. In converters that can act on both sides of the indefinite length sheet, it is not necessary to perform the roll-up.

Figure 3C:
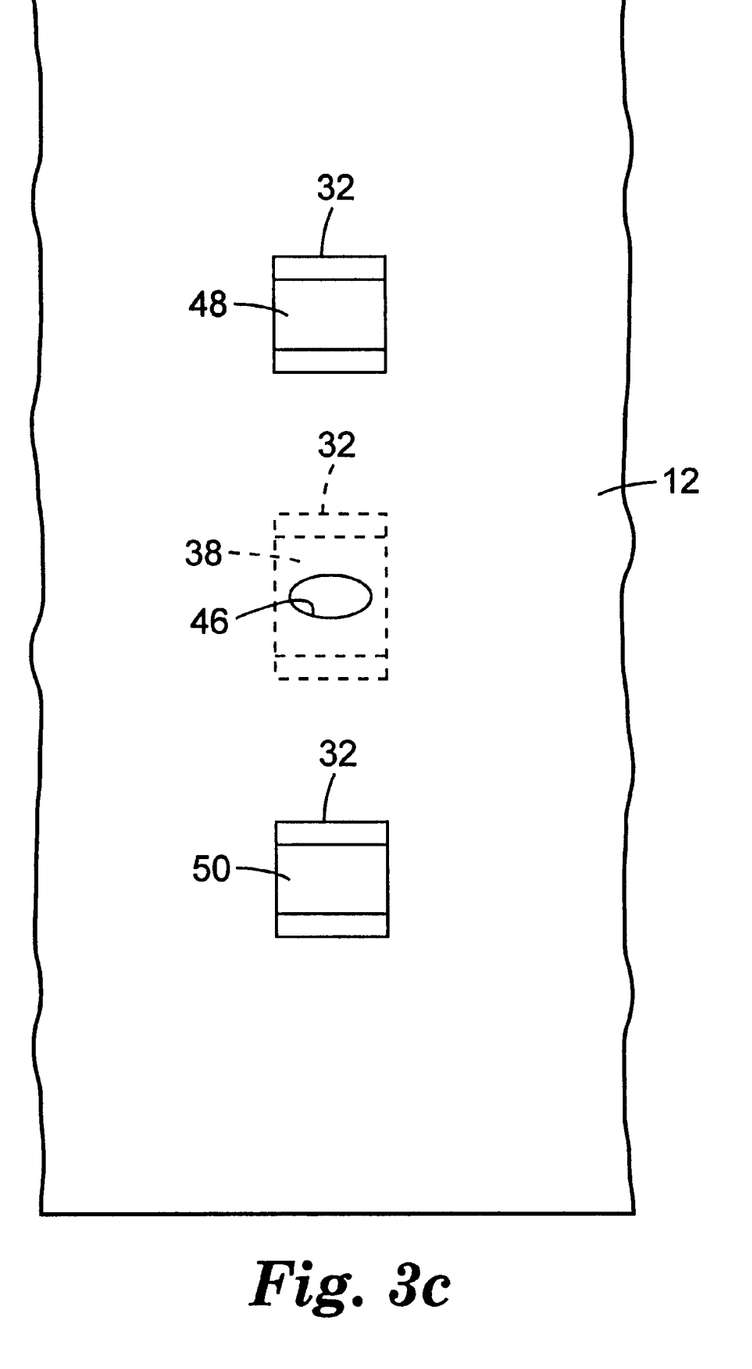

In FIG. 3c, two additional strips of transfer adhesive 48 and 50, similar in construction to strip 38 have been adhered to the indefinite length web. Note that these are on the opposite side of the sheet 12 from strip 38.

Figure 3D:
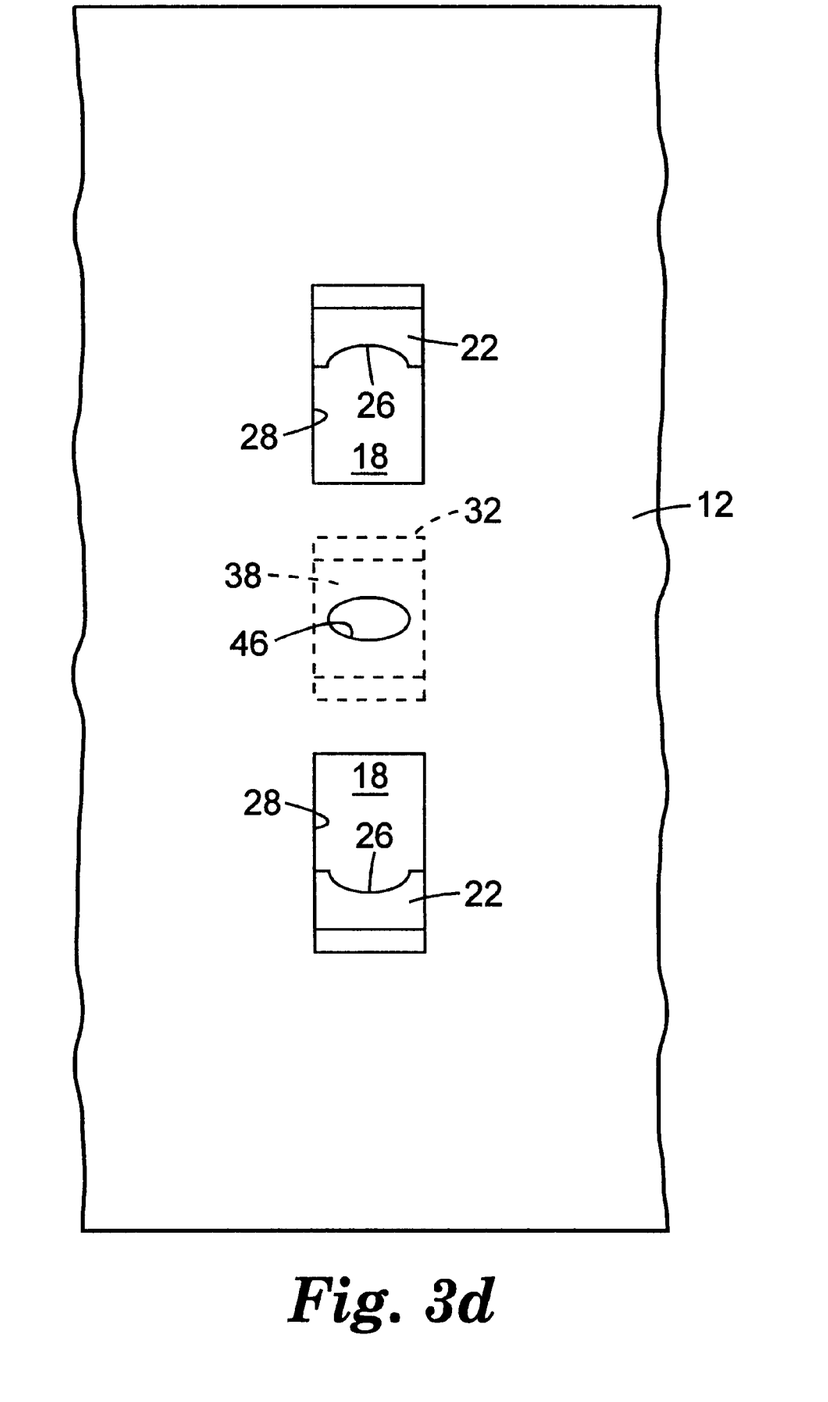

In FIG. 3d, a die cutter has just cut two apertures 18 and created two mirror images of curved portion 26. Strips 48 and 50 have been converted into two copies of first field of skin compatible adhesive 22.

Figure 3E:
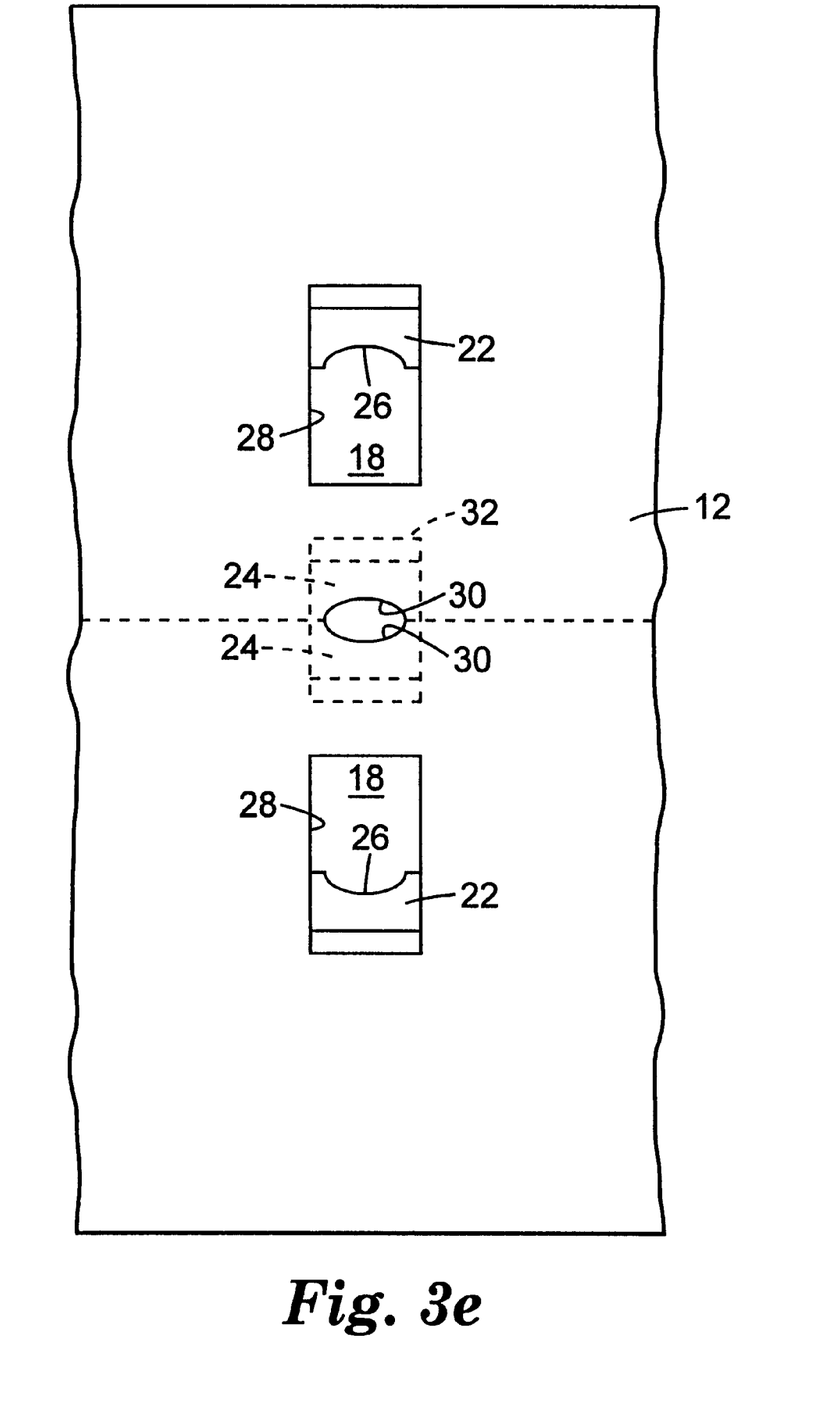

In FIG. 3e, a slitter has just sliced the indefinite length sheet 12 down the centerline, creating mirror imaged sections that are ready to be cut off to form a pair of drapes 10. Once strip 38 has been slit, opening 46 is divided into the two curved portions 30 on two facing drapes, and strip 38 is divided into two second fields of skin compatible adhesive 24 on these facing drapes.

Figure 3F:
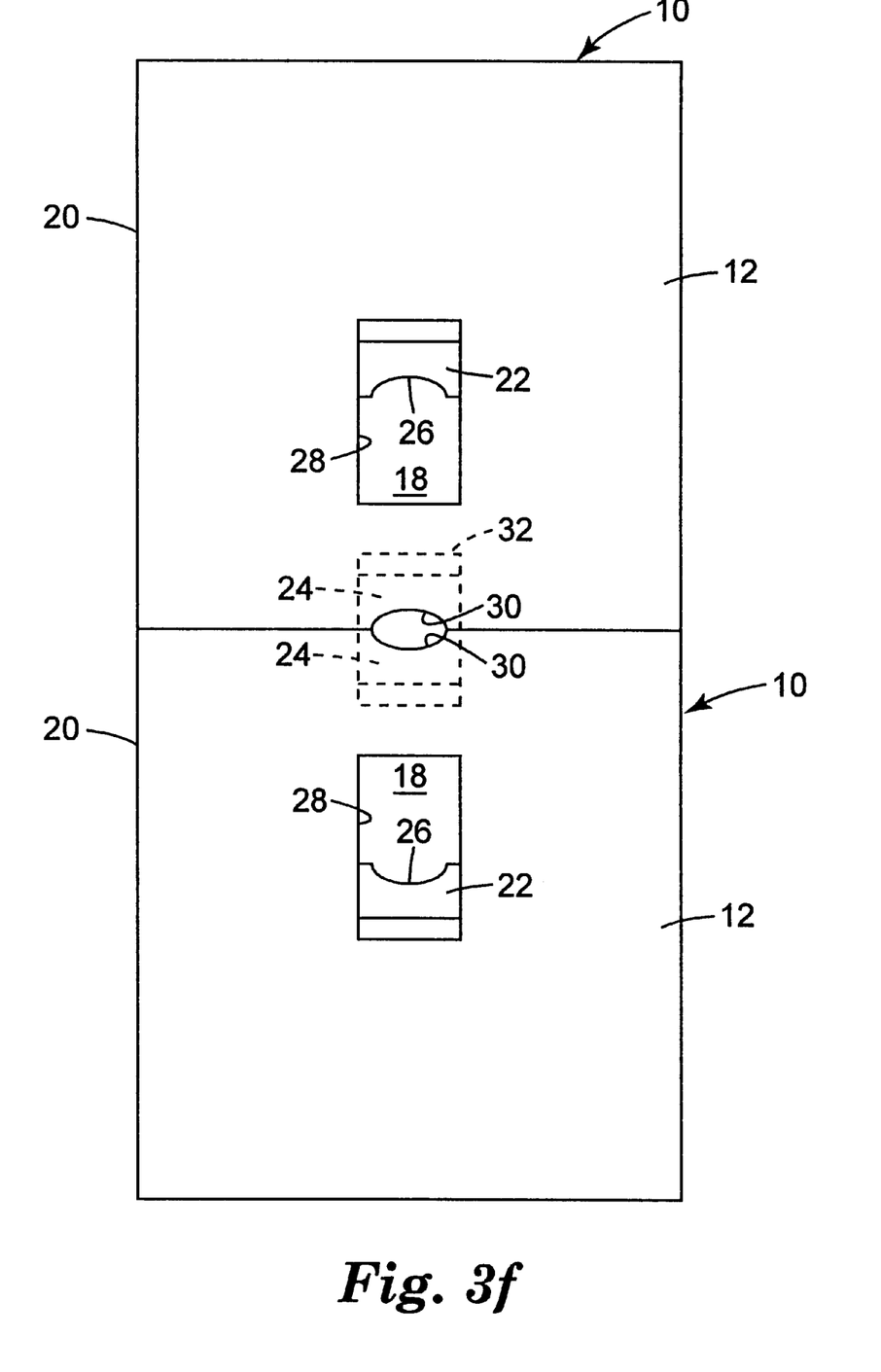

In FIG. 3f, a cutter has just sheeted off two mirror imaged drapes 10 from the indefinite length material that are ready to be folded, packaged, and sterilized for the customer.

Figure 4A:
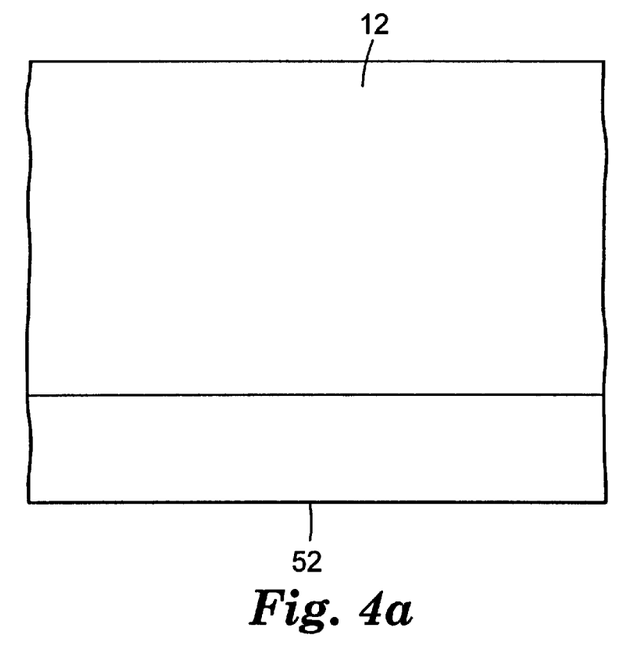
FIGS. 4a–4f are top views of a representative section of an indefinite length of sheet material at sequential stages of a "one-up" manufacturing scheme for the ophthalmic drape.

Referring now to FIGS. 4a–4f, top views of a representative section of an indefinite length web at sequential stages of a "one-up" manufacturing process for the ophthalmic drape 10. In FIG. 4a, an indefinite length of sheet material 12, conveniently 18 inches (45.7 cm) wide, has been folded at fold line 52. Not coincidentally, fold line 52 is approximately where the practitioner will eventually place fold line 34.

Figure 4B:
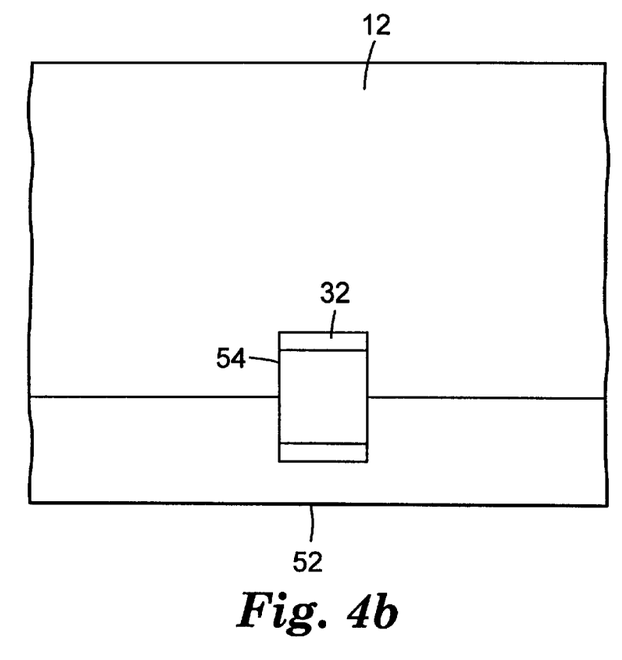
Figure 4C:
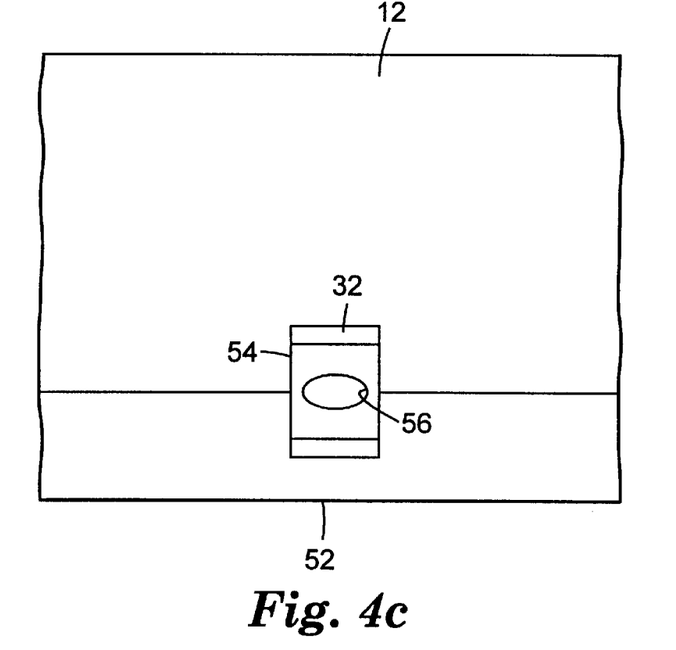
Figure 4D:
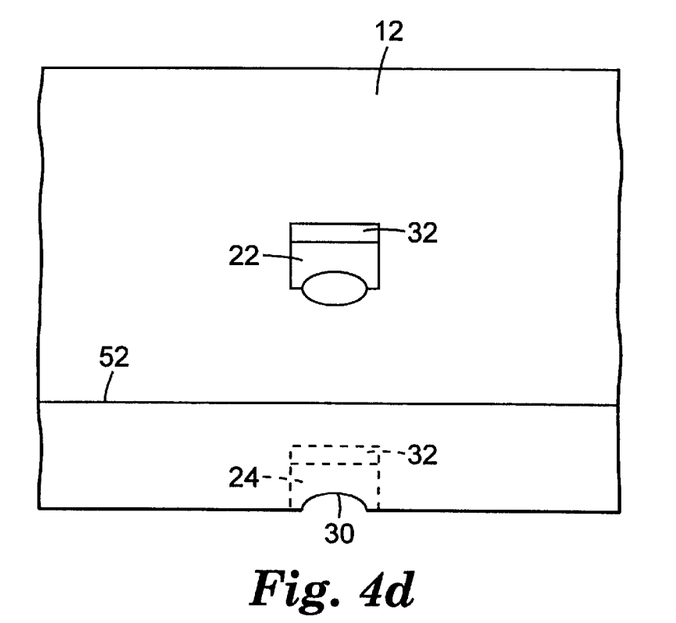

In FIG. 4b, the indefinite length of sheet 12 has had adhered to it a strip 54 of adhesive with a release liner 32 adhered to it in a manner similar to strip 38 discussed above. Strip 54 is placed partly on and partly off the folded edge. In FIG. 4c, an opening 56 has been die cut into the web within strip 54. In FIG. 4d, the folded edge has been slit and the indefinite length of sheet 12 has been unfolded again, creating from strip 54 the first and second fields of skin compatible adhesive 22 and 24, and curved portion 30.

Figure 4E:
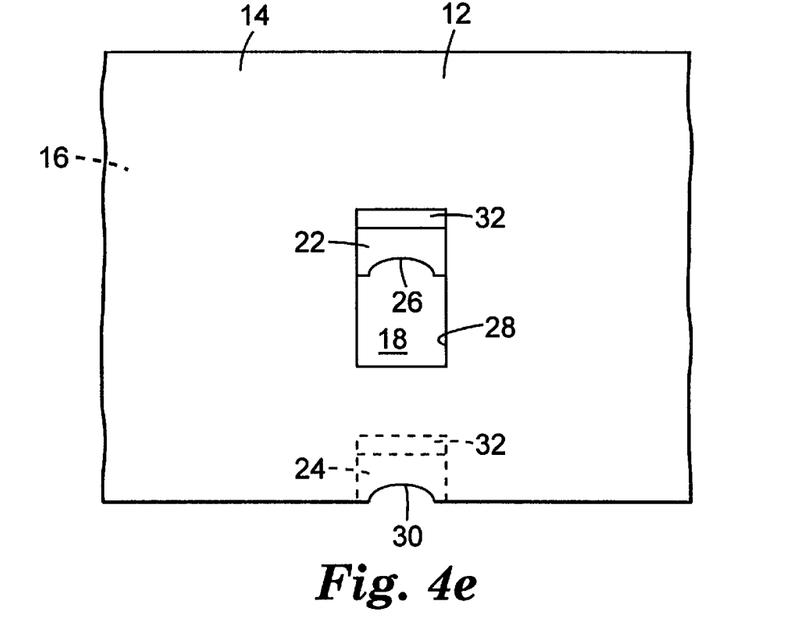
Figure 4F:
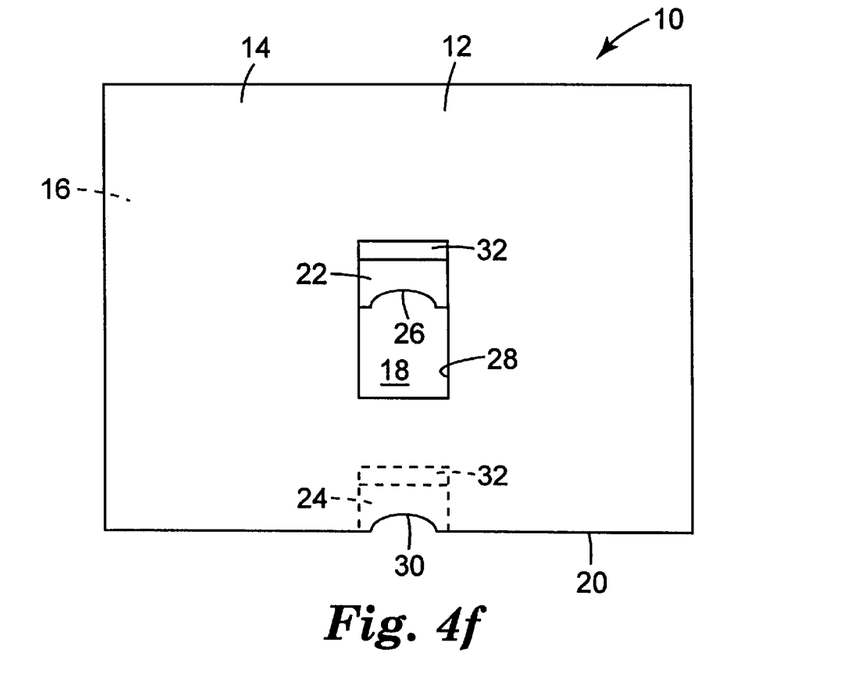

In FIG. 4e, a die cutter has just cut aperture 18 with its margin 28 and curved portion 26. In FIG. 4f, a cutter has just sheeted off the finished drape 10 from the indefinite length of sheet material 12, which drape 10 is then ready to be folded, packaged, and sterilized for the customer.

U.S. patent application Ser. No. 08/941,21 filed on the same date as this application by Yolla B. Levitt, Dennis L. Baker, Camille M. Hildebrandt, Mary K. Reed and Robert A. Davis (Attorney Docket No. 53660USA3A) on Ophthalmic Drape with Tear Line and Method is hereby incorporated herein by reference.

As various changes could be made in the above constructions and methods without departing from the scope of the invention as defined in the claims, it is intended that all matter contained in the above description or shown in the accompanying drawings be interpreted as illustrative and not in a limiting sense.

What is claimed is:

1. An ophthalmic drape for application to the upper and lower eyelids of an eye of a patient, the drape comprising:
    a sheet having a first and a second side, a periphery, and an aperture spaced from the periphery of the sheet;
    a first field of skin compatible adhesive contacting a portion of the first side of the sheet adjacent the aperture; and
    a second field of skin compatible adhesive contacting a portion of the second side of the sheet adjacent only one edge portion of the periphery of the sheet.

2. The An ophthalmic drape for application to the upper and lower eyelids of an eye of a patient, the drape comprising:
    a sheet having a first and a second side, a periphery, and an aperture spaced from the periphery of the sheet, the aperture having a curved portion approximating an eyelid;
    a first field of skin compatible adhesive contacting a portion of the first side of the sheet adjacent the aperture; and
    a second field of skin compatible adhesive contacting a portion of the second side of the sheet adjacent the periphery of the sheet, the periphery being defined in part by an edge portion adjacent the second field of skin compatible adhesive, the edge portion having a concave curved shape approximating an eyelid.

3. The ophthalmic drape according to claim 2 further comprising
    a first release liner adhered to the first field of skin compatible adhesive; and
    a second release liner adhered to the second field of skin compatible adhesive.

4. The ophthalmic drape according to claim 3 wherein the first and second sides of the sheet define a generally rectangular shape.

5. The ophthalmic drape according to claim 4 wherein the sheet is formed of polymeric film material.

6. A method of applying an ophthalmic drape to the upper and lower eyelids of an eye of a patient, the method comprising the following steps:
    (a) providing a surgical drape comprising
    a sheet having a first side, a second side, a periphery, and an aperture spaced from the periphery of the sheet;
    a first field of skin compatible adhesive contacting a portion of the first side of the sheet adjacent the aperture; and
    a second field of skin compatible adhesive contacting a portion of the second side of the sheet adjacent the periphery of the sheet;
    (b) adhering one of the fields of skin compatible adhesive to one of the eyelids; and
    (c) folding the surgical drape so that the other field of skin compatible adhesive is turned towards the patient; and
    (d) adhering the other field of skin compatible adhesive to the other eyelid.

7. The method according to claim 6 wherein:
    the aperture has a first curved portion approximating the eyelid,
    the periphery is defined in part by a edge portion adjacent the second field of skin compatible adhesive, the edge portion having a concave curved shape approximating the eyelid; and
    the step (b) of adhering one of the fields of skin compatible adhesive to one of the eyelids and the step (d) of adhering the other field of skin compatible adhesive to the other eyelid including placing one of the curved portion and the edge portion on one of the upper and lower eyelids, and placing the other of the curved portion and the edge portion on the other of the upper and lower eyelids.

8. The method according to claim 7 wherein the drape further comprises a first release liner adhered to the first field of skin compatible adhesive; and a second release liner adhered to the second field of skin compatible adhesive; the method further comprising the step of removing the first release liner from the first field of skin compatible adhesive and the step of removing the second release liner from the second field of skin compatible adhesive.

9. The method according to claim 7 wherein the step (b) of adhering one of the fields of skin compatible adhesive to one of the eyelids and the step (d) of adhering the other field of skin compatible adhesive to the other eyelid include placing the curved portion on the upper eyelid, and placing the edge portion on the lower eyelid.

10. A method of making an ophthalmic drape from an indefinite length web having first and second sides, a longitudinal direction and a width, the method comprising the following steps:
    (a) applying a first field of skin compatible adhesive to the first side of the web;
    (b) cutting a first opening through the first field of skin compatible adhesive and the web;
    (c) applying second and third fields of skin compatible adhesive to the second side of the web laterally spaced in opposite directions from the first field of skin compatible adhesive;
    (d) cutting a second opening through the second field of skin compatible adhesive and the web;
    (e) cutting a third opening through the third field of skin compatible adhesive and the web;
    (f) cutting the web in the longitudinal direction through the first opening;
    (g) cutting the web twice in the lateral direction along two cut lines spaced longitudinally in opposite directions from the first, second and third openings to form two ophthalmic drapes.

11. The method according to claim 10 wherein:
    the step (c) of applying second and third fields of skin compatible adhesive to the second side of the web laterally spaced in opposite directions from the first field of skin compatible adhesive includes laterally spacing the second and third fields of skin compatible adhesive a substantially equal distance from the first field of skin compatible adhesive; and
    step (f) and step (g) form substantially identical mirror image ophthalmic drapes.

12. The method according to claim 11 wherein the steps (b) of cutting a first opening through the first field of skin compatible adhesive and the web, (d) of cutting a second opening through the second field of skin compatible adhesive and the web, and (e) of cutting a third opening through the third field of skin compatible adhesive and the web each comprise:

die cutting the first, second and third openings.

13. The method according to claim 12 wherein the steps (b) of cutting a first opening through the first field of skin compatible adhesive and the web, (d) of cutting a second opening through the second field of skin compatible adhesive and the web, and (e) of cutting a third opening through the third field of skin compatible adhesive and the web each comprise:

cutting generally oval-shaped openings approximating generally the shape of an open eye.

14. The method according to claim 13 wherein the step of cutting generally oval-shaped openings approximating generally the shape of an open eye comprises cutting generally oval-shaped openings having a direction of elongation extending generally along the longitudinal direction of the web.

15. A method of making an ophthalmic drape from an indefinite length web having opposite major surfaces, opposite side edges and a lateral direction, the method comprising the following steps:

(a) folding one side edge of the web back on itself to form a flap folded over a main portion of the web with said one side edge overlapping the main portion of the web;

(b) applying skin compatible adhesive partly on the flap and partly on the main portion of the web with said one side edge dividing the adhesive into a first adhesive field on the main portion of the web and a second adhesive field on the flap;

(c) cutting an opening through the field of skin compatible adhesive, the flap and the main portion of the web, thus forming a first opening through the main portion and an indentation in the flap;

(d) unfolding the web;

(e) cutting the web in the lateral direction to form an ophthalmic drape having a first opening and a first adhesive field adjacent the opening along one major surface, and an indentation and a second adhesive field adjacent the indentation along the other major surface.

16. The method according to claim 15 further comprising the following step:

after the step (d) of unfolding the web, enlarging the first opening in the direction toward the indentation.

17. The method according to claim 16 wherein step (c) comprises cutting an oval-shaped opening.

18. The method according to claim 17 wherein the step (c) further comprising die cutting the opening.

19. The method according to claim 18 wherein step (c) comprises applying a strip of transfer adhesive or double stick patch to the web; the method further comprising cutting the strip of transfer adhesive or double stick patch to separate the first and second adhesive fields from one another before the step (d).

20. The method according to claim 19 wherein the step of die cutting the opening and the step of cutting the strip of transfer adhesive to separate the first and second adhesive fields from one another are performed in one integral operation with a single die.

* * * * *

UNITED STATES PATENT AND TRADEMARK OFFICE
CERTIFICATE OF CORRECTION

PATENT NO.: 6,070,587
DATED: Jun. 6, 2000
INVENTOR(S): Levitt et al.

It is certified that error appears in the above-identified patent and that said Letters Patent is hereby corrected as shown below:

Column 7, line 24, delete the word "The".

Signed and Sealed this

Eighth Day of May, 2001

Attest:

NICHOLAS P. GODICI

Attesting Officer

Acting Director of the United States Patent and Trademark Office